(12) United States Patent
Weber et al.

(10) Patent No.: US 9,345,656 B2
(45) Date of Patent: May 24, 2016

(54) ACRYLIC POLYMER

(75) Inventors: Dirk Weber, Basel (CH); John J. Geurts, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 13/988,869

(22) PCT Filed: Dec. 1, 2011

(86) PCT No.: PCT/EP2011/071573
§ 371 (c)(1),
(2), (4) Date: Aug. 12, 2013

(87) PCT Pub. No.: WO2012/072774
PCT Pub. Date: Jun. 7, 2012

(65) Prior Publication Data
US 2013/0344019 A1    Dec. 26, 2013

(30) Foreign Application Priority Data
Dec. 2, 2010   (EP) .................................... 10193512

(51) Int. Cl.
*A61Q 5/06*       (2006.01)
*A61K 8/81*       (2006.01)
*C08F 220/18*    (2006.01)
*C08F 220/06*    (2006.01)

(52) U.S. Cl.
CPC ................ *A61K 8/8152* (2013.01); *A61Q 5/06* (2013.01); *C08F 220/18* (2013.01); *C08F 220/06* (2013.01)

(58) Field of Classification Search
None
See application file for complete search history.

(56) References Cited

U.S. PATENT DOCUMENTS

| | | |
|---|---|---|
| 4,425,326 A | 1/1984 | Guillon et al. |
| 2010/0178442 A1 | 7/2010 | O'Brien et al. |

FOREIGN PATENT DOCUMENTS

| | | | |
|---|---|---|---|
| GB | 2 073 229 | | 10/1981 |
| WO | WO 2011/058163 | * | 5/2011 |

OTHER PUBLICATIONS

International Search Report for PCT/EP2011/071573 mailed Feb. 20, 2012.

* cited by examiner

*Primary Examiner* — Jyothsna Venkat
(74) *Attorney, Agent, or Firm* — Nixon & Vanderhye P.C.

(57) ABSTRACT

The present invention relates to acrylic emulsion polymers as well as to their use in hair care preparations such as in particular in hair styling preparations.

21 Claims, No Drawings

ACRYLIC POLYMER

This application is the U.S. national phase of International Application No. PCT/EP2011/071573 filed 1 Dec. 2011 which designated the U.S. and claims priority to EP 10193512.0 filed 2 Dec. 2010, the entire contents of each of which are hereby incorporated by reference.

The present invention relates to acrylic emulsion polymers as well as to their use in hair care preparations such as in particular in hair styling preparations.

Acrylate Copolymers such as e.g. Luvimer® (BASF), Balance® (Akzo Nobel) or Acudyne® (Rohm and Haas) are widely used in the Hair Care Industry as setting polymers for Aerosol and non-Aerosol Sprays. These polymers are prepared with emulsion polymerization technology which allows a good control over critical polymer parameters like molecular weight, particle size in the nm range and residual monomer content. However, there is an ongoing need for improved acrylic emulsion polymers which in particular dissolve quickly in low VOC (volatile organic compounds) compositions, exhibit a low viscosity and excellent high humidity curl retention, show fast drying properties and exhibit no tackiness during and after drying.

In addition the acrylic emulsion polymers should be readily formulated into cosmetic compositions such as in particular into hair care preparations in solvents or solvent mixtures with an increased water fraction. The preparations should have better sprayability coupled with good mechanical properties of the films formed. Besides the good compatibility with the customary cosmetic ingredients such as propellants the acrylic emulsion polymers should provide the hair with good setting and prolonged hold, have good wash-out properties and permit formulation as optically clear VOC 55 aerosols (i.e. with a VOC content of 55% by weight). In addition, the treated hair should have good haptic properties such as, for example, a good feel to the touch and being non-sticky.

It was therefore the object of the present invention to remedy the disadvantages of the prior art and to develop acrylic emulsion polymers which in particular give clear solutions within a short period of time in VOC 55 compositions, exhibit excellent high humidity curl retention, show fast drying properties and exhibit no tackiness during as well as after drying.

Surprisingly, it has been found that acrylic emulsion polymers obtainable from emulsion polymerization of methacrylic acid, n-butyl methacrylate and ethyl acrylate fulfill the above mentioned requirements.

Thus, the invention relates in a first embodiment to a process for the preparation of acrylic emulsion polymers comprising subjecting a monomer composition consisting of a mixture of methacrylic acid (MAA), ethyl acrylate (EA) and n-butyl methacrylate (BMA) to emulsion polymerization.

In a particular embodiment the monomer composition consists of a mixture of 10-30 wt.-% of methacrylic acid, 5-15 wt.-% of ethyl acrylate and 60-80 wt.-% of n-butyl methacrylate, such as in particular of 15-25 wt.-% of methacrylic acid, 8-12 wt.-% of ethyl acrylate and 65-75 wt.-% of n-butyl methacrylate, such as even more in particular of 18-23 wt.-% of methacrylic acid, 9-11 wt.-% of ethyl acrylate and 67-72 wt.-% of n-butyl methacrylate.

The term 'consisting of' as used according to the present invention means that the total amount of monomer ideally sum up to 100 wt.-%. It is however not excluded that small amount of impurities or additives may be present such as e.g. in amounts of less than 5 wt.-%, preferably less than 3 wt.-% which are e.g. introduced via the respective raw materials.

In another embodiment, the invention relates to acrylic emulsion polymers obtainable by the process according to the invention.

Acrylic emulsion polymers according to the present invention will be available at DSM Nutritional products Ltd. under the Tradename TILAMAR® Fix A140 (INCI: acrylates copolymer, Chemical Name: polymer with 2-methyl-2-propenoic acid, butyl 2-methyl-2-propenoate, and ethyl 2-propenoate, CAS Number: 26715-43-5).

The acrylic emulsion polymers according to the invention are prepared by emulsion polymerization methods according to known methods as outlined below and illustrated in the examples.

The method of free-radically initiated aqueous emulsion polymerization has been described previously on many occasions and is therefore sufficiently known to the person skilled in the art [cf. e.g. Encyclopedia of Polymer Science and Engineering, Vol. 8, pages 659 to 677, John Wiley & Sons, Inc., 1987; D. C. Blackley, Emulsion Polymerization, pages 155 to 465, Applied Science Publishers, Ltd., Essex, 1975; D. C. Blackley, Polymer Latices, 2.sup.nd Edition, Vol. 1, pages 33 to 415, Chapman & Hall, 1997; H. Warson, The Applications of Synthetic Resin Emulsions, pages 49 to 244, Ernest Benn, Ltd., London, 1972; D. Diederich, Chemie in unserer Zeit [Chemistry of our Time] 1990, 24, pages 135 to 142, Verlag Chemie, Weinheim; J. Piirma, Emulsion Polymerization, pages 1 to 287, Academic Press, 1982; F. Holscher, Dispersionen synthetischer Hochpolymerer [Dispersions of Synthetic High Polymers], pages 1 to 160, Springer-Verlag, Berlin, 1969 and DE-A 40 03422]. The free-radically initiated aqueous emulsion polymerization is usually carried out by dispersely distributing the monomers, usually with co-use of dispersants, in the aqueous medium, and polymerizing using at least one free-radical polymerization initiator.

Suitable free-radical polymerization initiators for the free-radical aqueous emulsion polymerization according to the invention are all those which are able to trigger a free-radical aqueous emulsion polymerization. These may in principle be either peroxides or azo compounds. Redox initiator systems are of course also suitable. Peroxides which may be used are, in principle, inorganic peroxides, such as hydrogen peroxide or peroxodisulfates, such as the mono- or di-alkali metal or ammonium salts of peroxide disulfuric acid, for example, its mono- and di-sodium, -potassium or ammonium salts or organic peroxides, such as alkyl hydroperoxides, for example tert-butyl, p-menthyl or cumyl hydroperoxide, tert-butyl perpivalate, and dialkyl or diaryl peroxides, such as di-tert-butyl or di-cumyl peroxide, 2,5-dimethyl-2,5-di(t)butyl-peroxy (hexane) or dibenzoyl peroxide.

The azo compounds used are essentially 2,2'-azobis(isobutyronitrile), 2,2'-azobis(2,4-dimethylvaleronitrile) and 2,2'-azobis(amidinopropyl)di hydrochloride (AIBA, corresponds to V-50™ from Wako Chemicals), 1,1'-azobis(1-cyclohexanecarbonitrile), 2,2'-azobis(2-amidinopropane) salts, 4,4'-azobis(4-cyanovaleric acid) or 2-(carbamoylazo)isobutyronitrile.

Suitable oxidizing agents for redox initiator systems are essentially the abovementioned peroxides. Corresponding reducing agents which may be used are sulfur compounds with a low oxidation state, such as alkali metal sulfites, for example potassium and/or sodium sulfite, alkali metal hydrogensulfites, for example potassium and/or sodium hydrogen sulfite, alkali metal metabisulfites, for example potassium and/or sodium metabisulfite, formaldehyde sulfoxylates, for example potassium and/or sodium formaldehyde sulfoxylate, alkali metal salts, specifically potassium and/or sodium salts, of aliphatic sulfinic acids (i.e. Bruggolite® FF6) and alkali metal hydrogen sulfides, such as, for example, potassium and/or sodium hydrogen sulfide, salts of polyvalent metals, such as iron(II) sulfate, iron(II) ammonium sulfate, iron(II) phosphate, enediols, such as dihydroxymaleic acid, benzoin and/or (i-) ascorbic acid, and reducing saccharides, such as sorbose, glucose, fructose and/or dihydroxyacetone.

The initiators are usually used in amounts up to 10% by weight, preferably 0.02 to 5% by weight, based on the monomers to be polymerized.

Surfactants can be utilized in order to assist the dispersion of the polymer in water. Suitable surfactants include but are not limited to conventional anionic and/or non-ionic surfactants and mixtures thereof such as Na, K and $NH_4$ salts of dialkylsulphosuccinates, Na, K and $NH_4$ salts of sulphated oils, Na, K and $NH_4$ salts of alkyl sulphonic acids, Na, K and $NH_4$ alkyl sulphates, alkali metal salts of sulphonic acids; fatty alcohols, ethoxylated fatty acids and/or fatty amides, and Na, K and $NH_4$ salts of fatty acids such as Na stearate and Na oleate. Other anionic surfactants include alkyl or (alk)aryl groups linked to sulphonic acid groups, sulphuric acid half ester groups (linked in turn to polyglycol ether groups), phosphonic acid groups, phosphoric acid analogues and phosphates or carboxylic acid groups. Non-ionic surfactants include polyglycol ether compounds and preferably polyethylene oxide compounds as disclosed in "Non-Ionic Surfactants—Physical Chemistry" edited by M. J. Schick, M. Decker 1987. The amount of surfactant used is preferably 0 to 15 wt.-% by, more preferably 0 to 8 wt-%, still more preferably 0 to 5% wt.-%, especially 0.1 to 3 wt-% and most especially 0.3 to 2 wt-% on the total weight of vinyl monomers required.

Chain transfer agent may be added to control the molecular weight. Suitable chain transfer agents include mercaptans such as n-dodecylmercaptan, n-octylmercaptan, t-dodecylmercaptan, mercaptoethanol, iso-octyl thioglycolate, $C_2$ to $C_8$ mercapto carboxylic acids and esters thereof such as 3-mercaptopropionic acid and 2-mercaptopropionic acid. Mixtures of two or more regulators may also be used.

Preferably 0.05 to 5 wt-%, more preferably 0.1 to 3 wt-% and most preferably 0.1 to 1 wt-% of chain transfer agent based on the weight of vinyl monomers required is used. The alkanethiols are usually added to the polymerization together with the monomers.

If, in the polymerization, thiols are used, a subsequent hydrogen peroxide treatment could be required in order to obtain polymers with a neutral odor.

The emulsion polymerization usually takes place with the exclusion of oxygen, for example under a nitrogen or argon atmosphere, at temperatures in the range from 20 to 200° C. Polymerization temperatures in the range from 50 to 130° C., in particular 70 to 95° C. are advantageous.

The polymerization can be carried out batch-wise, semi-continuously or continuously. The polymerization and the monomer and regulator feed are often carried out semi-continuously by the feed method. Preferably, at least some of the monomers, initiators and, if appropriate, regulators are metered into the reaction vessel uniformly throughout the polymerization. However, it is also possible to have an initial charge of the monomers and the initiator in the reactor and to polymerize them, with cooling if appropriate. Another option is to carry out the polymerization using seed latex prepared from the polymers to be polymerized in the first polymerization phase. The remainder of the monomer mixture is added, preferably by the feed method.

The polymerization reaction advantageously takes place until the monomer conversion is >95% by weight, preferably >98% by weight or >99% by weight.

It is often useful if the aqueous polymer dispersion obtained is subjected to an after-polymerization step in order to reduce further the amount of unreacted monomer. This measure is known to the person skilled in the art (for example EP-B 3957, EP-B 28348, EP-B 563726, EP-A 764699, EP-A 767180, DE-A 3718520, DE-A 3834734, DE-A4232194, DE-A 19529599, DE-A 19741187, DE-A 19839199, DE-A 19840586, WO 95/33775 or U.S. Pat. No. 4,529,753). It is of course also possible to subject the aqueous polymer dispersion obtained to an inert-gas and/or steam stripping, likewise known to the person skilled in the art, before or after the after-polymerization step. This stripping operation preferably takes place after the after-polymerization step. As is described in EP-A 805169, partial neutralization of the dispersion to a pH in the range from 5 to 7, preferably to a pH in the range from 5.5 to 6.5, is advantageous before the physical deodorization.

If applicable, due to a low monomer content after preparation, these possible additional steps can be omitted and the dispersions can be further used as such providing an economical advantage.

In a preferred embodiment, the aqueous polymer dispersion obtained is subjected to a post initation (post treatment/after-polymerization) using t-butyl hydroperoxide with iso-ascorbic acid or t-butyl hydroperoxide with aliphatic sulfinic acids (i.e. Bruggolite® FF6) in water. Particular preferred is a post-treatment of t-butyl hydroperoxide with aliphatic sulfinic acids (i.e. Bruggolite® FF6) as this reduces possible discoloration of the emulsion polymer as such or when dissolved in the end formulation.

The aqueous dispersion obtained from emulsion polymerization (eventually comprising a post treatment step) can either be incorporated directly into an aqueous, aqueous-alcoholic or alcoholic cosmetic preparation, for example a hair-styling preparation, or drying of the dispersion takes place, e.g. spray-drying or freeze-drying, so that the acrylic emulsion polymer can be used and processed in the form of powder.

In an advantageous embodiment, the aqueous dispersion obtained from the emulsion polymerization process, wherein the process preferably encompasses an after-polymerization step, is used as such for the intended application. The solid content of the aqueous dispersion can be adjusted, if desirable, by addition or removal of water. In a particular embodiment of the invention, the polymer solid content of the aqueous dispersion is in the range of 5 to 70 wt.-%, such as in the range of 20 to 60 wt.-% or 30 to 60 wt.-% such as in particular in the range of 35-45 wt.-%. The aqueous dispersion furthermore advantageously contains a preservative in order to enhance the shelf life such as in particular a broad-spectrum bactericide. Advantageously the preservative is methylisothiazolinone [CAS 2682-20-4] and is used at a concentration level of about 50 ppm or less, such as at a concentration level of about 1 to 50 ppm and in particular at a concentration level of about 30-50 ppm. Advantageously the concentration level of methylisothiazolinone in the dispersion is about 50 ppm. methylisothiazolinone is e.g. available as 9.5% methylisothiazolinone formulation in water as NEOLONE™ 950 at DOW.

Thus, the invention also relates to an aqueous dispersion of an acrylic emulsion polymer according to the invention, wherein the dispersion has a polymer solid content in the range of 30 to 60 wt.-%, such as in particular in the range of 35 to 45 wt.-%. In a preferred embodiment this dispersion further contains methylisothiazolinone, in particular in an amount of about 30 to 50 ppm. In a very particular embodiment the aqueous dispersion of an acrylic emulsion polymer according to the invention has a polymer solid content in the range of 35 to 45 wt.-% such as 40 wt.-% and a methylisothiazolinone content of about 50 ppm.

The acrylic emulsion polymers are usually partially or completely neutralized, expediently to 5 to 100%, or often to 30 to 95%, using an alkali metal hydroxide or preferably using an amine. In a preferred embodiment, the polymers are partially neutralized, and in a particularly preferred embodiment completely neutralized.

The neutralization is advantageously carried out with a mono-, di- or trialkanolamine having 2 to 5 carbon atoms in the alkanol radical, which is present in etherified form if appropriate, for example mono-, di- and triethanolamine, mono-, di- and tri-n-propanolamine, mono-, di- and triisopropanolamine, 2-amino-2-methyl-1-propanol and di(2-methoxyethyl)amine, an alkanediolamine having 2 to 5 carbon atoms, for example 2-amino-2-methylpropane-1,3-diol and 2-amino-2-ethylpropane-1,3-diol, or a primary, secondary or tertiary alkylamine having a total of 5 to 10 carbon atoms, for example N,N-diethylpropylamine or 3-diethylamino-1-propylamine Good neutralization results are often obtained with 2-amino-2-methyl-1-propanol, triiso-propanolamine, triethanolamine, tromethamine, 2-amino-2-ethylpropane-1,3-diol or 3-diethylamino-1-propylamine such as particularly with 2-amino-2-methyl-1-propanol which is e.g. available as AMP 95 at DOW.

Suitable alkali metal hydroxides for the neutralization are primarily sodium hydroxide, or potassium hydroxide and ammonium hydroxide.

Also suitable for the neutralization are aqueous buffer solutions, such as, for example, buffers based on alkali metal or ammonium carbonate, bicarbonate, or citrate.

The neutralizing agents are preferably added in the form of a dilute aqueous solution to the acrylic polymer emulsion.

In a particularly preferred embodiment the acrylic emulsion polymers according to the invention are completely neutralized, in particular with 2-amino-2-methyl-1-propanol.

The pH can, if appropriate, also be adjusted by adding a buffer solution, preference being given to buffers based on alkali metal or ammonium carbonate or hydrogen carbonate.

The polymer solids content of the aqueous acrylic polymer emulsion accessible according to the process of the present invention is frequently 5 to 70% by weight, often 20 to 60% by weight, or 30 to 60% by weight such as in particular 40-45% in the most preferred case and can easily be adjusted by addition or removal of water.

The acrylic emulsion polymers according to the invention have a molecular weight between 30-500 kDalton, more preferably 50-250 kD and most preferred between 75 and 200 kDalton such as in the range of 100 to 150 kDalton, and a glass transition temperature between 40 and 140° C., more preferably between 55 and 130° C. and most preferred between 70-120° C. such as e.g. between 70 and 100° C. Due to high Tg of the acrylic emulsion polymers no anti-caking agent is needed to prevent the polymers from sticking during storage even at elevated temperature if provided in powder form. Advantageously the emulsion polymers according to the invention have a molecular weight between 75-200 kDalton and a Tg in the range of 70-120° C. such as in particular a molecular weight between 100-150 kDalton and a Tg in the range of 70-100° C.

The glass transition temperature $T_g$ is the limit at which, according to G. Kanig (Kolloid-Zeitschrift & Zeitschrift fur Polymere, Vol. 190, page 1, equation 1) the polymer changes from a glassy, brittle state to a rubbery state. Tg values of polymers may e.g. be determined experimentally using techniques such as differential scanning calorimetry DSC.

The total residual monomer content of the emulsion polymer according to the present invention is preferably below 500 ppm, more preferably below 350 ppm, most preferably below 200 ppm. The total amount of residual n-butyl methacrylate (BMA) is preferably below 300 ppm, more preferably below 200 ppm, most preferably below 150 ppm. The total amount of residual methacrylic acid (MAA) is preferably below 300 ppm, more preferably below 200 ppm, most preferably below 150 ppm. The total amount of residual ethyl acrylate (EA) is preferably below 200 ppm, more preferably below 100 ppm, most preferably below 50 ppm.

The viscosity (dynamic 25°) of the emulsion polymer according to the present invention is preferably selected in the range of 5-100 cPS [mPa·s] such as more preferably in the range of 10-70 cPs [mPa·s].

The acid value is preferably selected in the range of 80-200 mg KOH/g such as more preferably in the range of 120-150 mg KOH/g.

After neutralization e.g. with 2-amino-2-methyl-1-propanol (AMP), the acrylic emulsion polymers according to the invention exhibit an excellent solubility in low water VOC formulations such as e.g. VOC 55 compositions making them suitable for a wide range of applications allowing in particular the formulation of cosmetic compositions with an increased water content.

Furthermore, the acrylic emulsion polymers according to the invention exhibit a good compatibility with cosmetic ingredients making them especially suitable for cosmetic applications.

Thus, the invention in a further embodiment relates to cosmetic compositions comprising at least one acrylic emulsion polymers according to the invention and a cosmetically acceptable carrier. The term "cosmetic composition" as used herein refers in particular to cosmetic compositions that can be topically applied to mammalian keratinous tissue such as e.g. human skin or scalp.

The term "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic compositions as disclosed in A. Domsch, "Cosmetic Compositions", Verlag für chemische Industrie (ed. H. Ziolkowsky), 4$^{th}$ edition, 1992.

The term cosmetically acceptable carrier refers to all carriers and/or excipients and/or diluents conventionally used in cosmetic compositions.

The amount of the at least one acrylic emulsion polymers according to the present invention in the cosmetic compositions may easily be chosen by a person skilled in the art in an amount suitable for the desired application. Preferably, a concentration (based on solids) of 0.01-20 wt. %, most preferred of 0.05-10 wt. % based on the total weight of the cosmetic composition is used.

Next to their excellent solubility and compatibility with cosmetic ingredients, the acrylic emulsion polymers according to the invention furthermore show excellent hair styling properties such as e.g. excellent high humidity curl retention making them in particular suitable for hair care applications. Thus, the acrylic emulsion polymers according to the invention are advantageously used in hair care preparations such as in particular in hair styling preparations.

Hair care preparations which may be mentioned are hair treatments, hair lotions, hair rinses, hair emulsions, end fluids, neutralizing agents for permanent waves, hot-oil treatment preparations, conditioners, curl relaxers, styling wrap lotions, setting lotions, shampoos, hair waxes, pomades, hair mousses, hair colorants or hairsprays. Particular preference is given to the use of the acrylic emulsion polymers in hairstyling preparations which are advantageously in the form of spray preparations and/or hair mousses.

The acrylic emulsion polymers according to the invention are characterized in hair care preparations by their good compatibility with propellants such as n-propane, isopropane, n-butane, isobutane, n-pentane and mixtures thereof or dimethyl ether (DME) and in particular by the excellent sprayability as pump spray or aerosol. Thus, the hair care preparations according to the invention are in particular hair spray preparations further comprising a propellant such as in particular propane/butane or DME.

The acrylic emulsion polymers according to the invention are also very readily compatible with other additives customary in hair care, have a good hair-setting action, form films with very good mechanical properties and are characterized in that they cause virtually no sticking-together of the hair.

The amount of the acrylic emulsion polymers according to the present invention in hair care preparations such as in particular hair styling preparations is preferably selected within a concentration range of 0.01-20 wt.-%, more preferably within a concentration range of 0.1-10 wt. % such as in particular within a concentration range of 1 to 10 wt.-% based on the total weight of the hair care preparation.

The hair care preparations according to the present invention may be in the form of a (aerosol) spray, (aerosol) foam, gel, gel spray, cream, lotion, liquid or a wax. Hair sprays comprise as well aerosol sprays as pump sprays without propellant. Hair foams comprise as well aerosol foams as pump foams without propellant. Hair sprays and hair foams comprise mainly or exclusively water soluble or water dispersible components. If the components used in hair sprays or hair foams are water dispersible, then they may be in the form of micro dispersions with particle sizes of usually 1-350 nm, preferably 1-250 nm. The solid content of such preparations is typically in the range of 0.5 to 20 wt. % of the total weight of the preparation. Such micro dispersions normally do not need further emulsifiers or tensides for their stabilization. In particular the hair styling preparations according to the invention are in the form of styling creams, styling gels, liquid hair-setting preparations, hair foams or hairspray compositions.

Besides the freedom from odor, the acrylic emulsion polymers according to the invention yield excellent results in view of application properties for hair care preparations and in particular hair styling preparations. They dissolve in alcohols such as ethanol or isopropanol and in mixtures of these alcohols with water to form clear solutions. The clarity of the solutions is also obtained when the solutions are used in standard spray formulations together with propellants such as propane/butane or dimethyl ether. In particular, they can be formulated in aqueous low-VOC preparations with at most 55% by weight of volatile organic constituents (VOC 55 compositions) to give clear mixtures.

Thus, the invention also relates to hairspray compositions comprising an acrylic emulsion polymer according to the invention in an aqueous, aqueous-alcoholic or alcoholic solvent, wherein the concentration of the acrylic emulsion polymer (based on solids) is about 0.01-20 wt.-%, preferably about 0.05-10 wt.-% such as e.g. about 5 wt.-%. In particular, the composition is a 55% or less VOC (volatile organic compounds) pump spray composition, comprising preferably 0.1-10 wt.-% (based on solids) of the acrylic emulsion polymer of the invention, 55 wt.-% or less ethanol, 0-5 wt.-% adjuvants and the rest water. Particularly, the 55% or less VOC aerosol hair spray composition contains 0.1-10 wt.-%, preferably 1-7 wt.-% (based on solids) acrylic emulsion polymer, 25 wt.-% or less ethanol, and 40 wt.-% or less of propellant, preferably dimethyl ether (DME), 0-5 wt.-% adjuvants, preferably including a neutralizer and corrosion inhibitor, and the rest being water.

Furthermore, the invention relates to a 55 wt.-% or less VOC pump or aerosol hair spray composition containing 0.1-10 wt. % (based on solids) of the acrylic polymer emulsion which has an effective spray pattern and small particle size, forms clear, evenly spread films, a desirable high humidity curl retention property, good stiffness, and low tack and short drying times.

The hair-styling preparations such as e.g. the hairspray compositions according to the invention can be washed out of the hair without problems. Hair treated therewith has increased softness and a pleasant natural feel. The setting action is also good, making it possible, in principle, to reduce the required amount of film former in the hair-styling preparations.

The hair care preparations such as in particular the hair styling preparations may also contain other hair fixative resins, neutralizers, surfactants, solvents, propellants, other preservatives, thickeners, UV-filters and other additives usually employed in such preparations.

Other hair fixative resins may optionally be added to the hair care preparations to provide other properties which may be desired by the formulator, such as a "stiffer" hold of the hair. The other hair fixative resins may be soluble or insoluble in the hair styling preparation. The other hair fixative resins may be present in the hair styling preparation at a concentration of from 0.01 to 10.0 wt.-%, preferably from 0.1 to 7.0 wt.-%, based on the total weight of the hair styling preparation.

The other hair fixative resins which are suitable in the hair care preparation include for example butyl acrylate/ethyl acrylate/methacrylic acid copolymers; polyvinyl pyrrolidone, vinyl pyrrolidone/vinyl acetate compolymers; octylacrylamide/acrylates/butyl-aminoethylmethacrylate copolymers; vinylcaprolactam/vinylpyrrolidone/dimethylaminoethylmethacrylate copolymers; methacryloyl ethylbetaine/methacrylate copolymers; methacrylic acid/methacrylic ester copolymer; methacrylic acid/acrylic acid ester copolymers, alkylester of the copolymer of vinyl methyl ether and maleic anhydride; hydroxyethylcellulose quaternized with diallyl dimethyl ammonium chloride, quaternized vinyl pyrrolidone/dimethylaminoethylmethacrylate copolymer, or combinations thereof.

Neutralizers are preferably present in the hair care preparation when the hair fixative resins contain acidic groups, such as carboxylic acid groups, to promote solubility of the resin in the aqueous hair styling composition. For example, the acrylic hair fixative resin is preferably fully neutralized.

Bases which will neutralize the hair fixative resins include for example amines, alkali or alkaline earth metal hydroxides, ammonium hydroxide or combinations thereof. Suitable amine neutralizers include for example 2-amino-2-methyl propanediol, 2-amino 2-methyl propanol, N,N dimethyl 2-amino 2-methyl 1-propanol, mono-isopropanolamine, tri-isopropanolamine, ethanolamine, triethanolamine, morpholine or combinations thereof. Suitable alkali or alkaline earth metal hydroxides include for example sodium hydroxide potassium hydroxide, or combinations thereof. Preferably, the neutralizer is selected from the group consisting of 2-amino 2-methyl propanediol, 2-amino-2-methyl propanol, N,N dimethyl 2-amino 2-methyl propanol, potassium hydroxide, triethanolamine, triisopropanolamine, or combinations thereof.

The amount of neutralizer added to the hair care preparation is preferably that amount to provide solubility of the hair fixative resin in the hair styling composition. Preferably, in a hair styling preparation containing 35 weight percent or less VOC, from 40 to 100 mole percent of the acid groups on the hair fixative resin are neutralized. For a VOC hair styling composition containing more than 35 weight percent VOC, preferably more than 50 mole percent of the acid groups on the hair fixative resin are neutralized.

One or more surfactants may be added to the hair care preparation. When surfactants are present in the hair care preparation, they are preferably present at a concentration of from 0.001 to 1.0 weight percent, based on the total weight of the composition. The surfactants which may be used in the hair care preparation include for example anionic, cationic, nonionic, or amphoteric surfactants. For example, suitable surfactants include PPG 28 Buteth 35, PEG 75 lanolin, perfluoropolymethyl isopropyl ether, octoxynol-9, PEG-25 hydrogenated castor oil, polyethylene terephthalate, polyethylene glycol 25 glyceryl trioleate, oleth-3 phosphate, PPG-5-ceteth-10 phosphate, PEG-20 methyl glucose ether, glycereth-7-triacetate, glycereth-7-benzoate, fatty acid ester of polysorbate (TWEEN), or n-alkyl substituted lactam such as n-octyl pyrrolidone, or combinations thereof.

One or more siloxane derivatives may be present in the hair care formulation. When they are used, they are preferably present in a concentration from 0.001 to 1.0 weight percent, based on the total weight of the composition. The siloxane derivatives include for example dimethicones, phenyl trimethicones, dimethiconols, amodimethicones, alkoxylated dimethicones e.g. PEG-12 dimethicone or methoxy PEG/PPG-7/3 aminopropyl dimethicone.

One or more solvents may be added to the hair care preparation of the present invention. The solvents may or may not be VOC. When solvents are added to the hair care preparation they preferably comprise 55 weight percent or less, and more preferably 100 weight percent or less, based on the total weight of the hair care preparation. Suitable solvents include for example $C_1$ to $O_{12}$ straight or branched chain alcohols such as methanol, ethanol, isopropanol, or propanol or combinations thereof.

In a hair care preparation such as in particular a hair styling preparation using an aerosol spray, one or more propellants are used. The propellants may or may not be VOC. Preferably, the propellants are used at a total concentration of from 10 to 70 wt.-%; and more preferably from 30 to 60 wt.-% based on the total weight of the hair care preparation. Propellants include for example n-butane, isobutane, dimethyl ether; dimethoxymethane, difluoroethane, chlorodifluoroethane, chlorodifluoromethane, other chlorofluorocarbons or combinations thereof. Preferred propellants are dimethyl ether, 1,1-difluoroethane, n-butane, isobutane or combinations thereof. These propellants are commercially available.

As stated previously, the total VOC in the hair care preparation, whether the VOC is a solvent or propellant, should be 80 wt.-% or less based on the total weight of the hair care preparation.

Preservatives which may be used in the hair care preparation include for example isothiazolones, benzyl alcohol, or imidazolidinylurea. The other preservatives are preferably used in an amount of about 0.001 to 1.0 wt.-% based on the total weight of the hair care preparation.

One or more thickeners may be desirable in a hair care preparation which is applied to the hair in form of a mousse or styling gel. Suitable thickeners include for example polycarboxylic acid thickeners such as acrylates/steareth-20 methacrylate copolymer, carbomers, acrylates copolymer, or acrylates $C_{10-30}$ acrylate crosspolymer; polyethoxylated urethane thickeners, or polyamide thickeners. Other suitable thickeners are based on natural polymers such as polysaccharides or polyamides and can be chemically modified. Such thickeners include for instance hydroxyethyl celluloses, hydroxypropyl celluloses, xathan gum, gelatine, agar-agar, carragenens, alginates or mixtures thereof. The thickeners are preferably used in an amount of about 0.001 to 5.0 wt.-% based on the total weight of the hair care preparation.

One or more light screening agents may be desirable in a hair care preparation according to the invention. The light screening agents are advantageously selected from UV-A, UV-B, UV-C and/or broadband filters such as in particular from the commercially available and widely used UV-filter substances octocrylene (PARSOL® 340), 4-methyl benzylidene camphor (PARSOL® 5000), ethylhexyl methoxycinnamate (PARSOL® MCX), ethylhexyl triazone (Uvinul® T-150), diethylhexyl butamido triazone (Uvasorb® HEB), 2,2'-methylene-bis-(6-(2H-benzotriazole-2-yl)-4-(1,1,3,3,-tetramethylbutyl)-phenol (Tinosorb® M), bis-ethylhexyloxyphenol methoxyphenyl triazine (Tinosorb® S), 2,2-(1,4-phenylene)bis-(1H-benzimidazol-4,6-disulfonic acid (NeoHeliopan® AP), 2-(4-Diethylamino-2-hydroxy-benzoyl)-benzoic acid hexylester (Uvinul® A plus), polysilicone-15 (PARSOL® SLX), 2-phenyl benzimidazole sulfonic acid (PARSOL® HS), ethylhexyl salicylate (PARSOL® EHS), homomenthyl salicylate (PARSOL® HMS), Benzophenone-3 (Uvinul® M 40), Benzophenone-4 (Uvinul® MS 40), PEG-25 PABA, as well as mixtures thereof.

The light screening agents are generally present in the compositions according to the invention in proportions ranging from 0.001 to 5 wt.-%, preferably ranging from 0.01 to 1 wt.-%, most preferably ranging from 0.02 to 0.5 wt.-% with respect to the total weight of the composition.

Additionally other additives, such as those commonly used by those skilled in the art may be added to the hair care preparation according to the invention. The other additives used in the hair care preparations will depend upon the type of hair care preparation desired. Other additives include for example fragrances; moisturizers such as sorbitol, propane diol, butylene glycol, glycerin, hydrolyzed silk protein, or hydrolyzed wheat protein; detangling aids such as panthenol; conditioning agents such as those disclosed in U.S. Pat. No. 5,164,177 emulsifiers; antistatic aids, extracts, proteins, vitamins, dyes, tints, colorants or combinations thereof. The other additives are typically present from 0.005 to 5 wt.-%; more preferably from 0.01 to 1 wt.-% based on total weight of the hair care preparation.

Additional other additives, as well as additional surfactants, solvents, other preservatives, and thickeners, which may be suitable in the hair care compositions may be found in the International Cosmetic Ingredients Dictionary, 5th Edition, 1993, published by the CTFA in Washington D.C.

The following examples are provided to further illustrate the processes and compositions of the present invention. These examples are illustrative only and are not intended to limit the scope of the invention in any way.

In the examples the following abbreviations or trade names are employed.

BMA=n-butyl methacrylate
EA=ethyl acrylate
MAA=methacrylic acid
SLES=ethoxylated sodium lauryl sulphate [30 wt % in water]

AMPS=ammonium persulfate
nDM=n-dodecyl mercaptan
i-AA=i-ascorbic acid
t-BHPO=t-butylhydroperoxide [70 wt % in water]

EXAMPLE 1

Preparation of MAA, EA, BMA Copolymer Emulsion

Initial charge: water (744 g), SLES (7.2 g)
Monomer feed: MAA (156 g), BMA (546 g), EA (78 g), nDM (1.6 g), water (346 g), SLES (44 g).
Initiator solution: AMPS (0.8 g), water (7 g)

The initial charge mixture was transferred to the reaction vessel, stirred under a nitrogen atmosphere and the temperature was raised to 80° C. The monomer feed was prepared and transferred to the feed vessel.

At a reactor vessel temperature of 80° C., 5% of monomer feed was added, followed by an addition of the initiator solution. After 5 minutes the monomer feed was started. The monomer feed was fed in 90 min. After the feed the reactor vessel was kept at 80° C. for 15 minutes.

A post reaction was conducted using t-BHPO and a solution of i-AA in water. The solids content was adjusted with water to 40%. The resulting emulsion polymer had a pH of 3.0, and a viscosity of 40 mPas. All viscosity measurements where made at 25° C., using spindle 1 at 160 rpm.

EXAMPLE 1(a)

Monomer feed MAA (190 g), BMA (530 g), EA (72 g); post treatment: t-BHPO/solution of Bruggolite® FF6 in water; solids content adjusted to 40%; pH: 2.8, viscosity: 17 mPas.

EXAMPLE 1(b)

Monomer feed MAA (140 g), BMA (530 g), EA (72 g); post treatment t-BHPO/solution of i-AA in water; solids content adjusted to 40%; pH: 3.4, viscosity: 28 mPas.

EXAMPLE 2

Solubility

The solubility of the acrylates copolymer emulsion according to example 1 in standard hair care preparations was determined by preparation of the formulations as indicated in table 1 according to standard procedures and determination of the turbidity with a HACH 2100 N IS Turbidimeter, 115 Vac according ISO 7027 (The threshold for turbidity is at NTU≥5. (NTU<5 means visibly clear solution)). Furthermore, the solutions were assessed visually.

TABLE 1

| Formulation | Composition | visual | NTU* |
|---|---|---|---|
| High VOC | 12.5% Acrylates Copolymer Emulsion<br>1.2% AMP-95<br>Ad. 100 Ethanol | clear | 0.9 |
| VOC 80 | 12.5% Acrylates Copolymer Emulsion<br>1.05% AMP-95<br>80% Ethanol<br>Ad. 100 Water | clear | 5 |
| VOC 55 | 12.5% Acrylates Copolymer Emulsion<br>1.05% AMP-95<br>55% Ethanol<br>Ad. 100 Water | clear | 2 |
| VOC 35 | 12.5% Acrylates Copolymer Emulsion<br>1.2% AMP-95<br>35% Ethanol<br>Ad. 100 Water | clear | 2.4 |

As to be seen, all values are equal or below the threshold for "crystal clear" NTU = 5 and the formulations are clear.

Additionally, the dissolution time (i.e. time until a clear solution is obtained) of the acrylate emulsion polymers according to the invention has been assessed compared to benchmark acrylate emulsion polymers. Thus, 5 g (based on solids) of the respective polymer are dispersed in a mixture of 55 g ethanol, 31.43 g of water and the calculated amount of AMP (AMP 2000 (95%)) for complete neutralisation as indicated in the table. The mixtures are stirred till they are clear and the required time for it is recorded.

TABLE 2

Dissolution times in VOC 55 compositions

| Product Name<br>[Supplier] | Monomer Composition | AMP<br>[g/g polymer] | Dissolution<br>Time |
|---|---|---|---|
| Amphomer ® [NStarch] | Octylacrylamide/Acrylates/<br>Butylaminoethyl Methacrylate<br>Copolymer | 0.192 | ~4 hours |
| Luvimer ® P100 [BASF] | Methacrylic acid, tert-Butyl<br>acrylate, Ethyl acrylate<br>Copolymer | 0.246 | ~20 min |
| Acudyne ™ 180<br>[Rohm&Haas] | Acrylates/Hydroxyesters<br>Acrylates Copolymer | 0.197 | ~30 min |
| Acudyne ™ DHR<br>[Rohm&Haas] | Acrylates/Hydroxyesters<br>Acrylates Copolymer | 0.180 | ~30 min |
| Balance ® 0/55 [NStarch] | Butyl acrylate, •Methacrylic acid, •Methyl<br>methacrylate copolymer | 0.141 | ~1 hour |
| TILAMAR ® Fix A140[1] | Methacrylic acid, Ethyl acrylate<br>and n-Butyl methacrylate<br>copolymer | 0.214 | within seconds |
| Acrylic emulsion polymer<br>according to example 1(a) | Methacrylic acid, Ethyl acrylate<br>and n-Butyl methacrylate<br>copolymer | 0.252 | within seconds |

TABLE 2-continued

Dissolution times in VOC 55 compositions

| Product Name [Supplier] | Monomer Composition | AMP [g/g polymer] | Dissolution Time |
|---|---|---|---|
| Acrylic emulsion polymer according to example 1(b) | Methacrylic acid, Ethyl acrylate and n-Butyl methacrylate copolymer | 0.200 | within seconds |

[1]Acrylic emulsion polymer according to example 1

As can be seen only the acrylic polymer emulsion according to the invention dissolves within seconds after the addition.

EXAMPLE 3

Viscosity

The viscosity of a 5 wt % (solids) acrylic emulsion polymer solution according to example 1 (100% neutralized with AMP) in ethanol/water (VOC 55) was determined by the peak hold test; shear stress: 10 Pa/25° C.; shear rate: 1/s; Cylinder: Ø60 mm 2° (acrylic 5864)

TABLE 3

Viscosity

| | Time [min] | | | | | | | | | |
|---|---|---|---|---|---|---|---|---|---|---|
| | 0.1 | 0.2 | 0.3 | 0.4 | 0.5 | 0.6 | 0.7 | 0.8 | 0.9 | 1.0 |
| Viscosities in [mPas] | 13.9 | 13.6 | 13.5 | 14.0 | 13.5 | 13.6 | 13.8 | 13.6 | 13.5 | 13.9 |

As to be seen the acrylic emulsion polymer solution exhibits a low viscosity.

EXAMPLE 4

High Humidity Curl Retention Test with TILAMAR® Fix A140

Hair Tresses (Kerling; Art. Nr. 826 500) are cut in switches of 2 cm width. Each switch is washed twice with 0.5 mL of a Cleansing Shampoo (10% Sodium Laureth Sulfate/4% Sodium Chloride): 30 s foaming, 90 s rinsing with warm water. The switches are combed 5 times and dried in a climate room at 20° C. and 65% relative humidity for at least 4 hours. The weight of the switches is standardized under these conditions for 2 g +/−0.2 g for hair (without rubber coating). Afterwards the switch is dampened with 1 g water, and evenly wetted with 0.3 g of polymer solution (5% solids in EtOH, 100% neutralized with AMP-95): application with syringe from root to tip and comb 5 times. Then, the switch is curled with a spiral curler of 12 mm diameter (Basler Haarkosmetik Art. 12939).

The curler with the hair is dried for 40 min at 45° C. Then, the curler is left in the climate room at 20° C./65% rel. humidity over night. The curl is removed carefully from the curler, lay at the table and the starting length $L_0$ is taken. Than, the curl is hung up at the rubber coating in the climate chamber at 20° C./90% rel. humidity, and the Length $L_t$ is taken after following times: 0 min, 15 min, 30 min, 45 min, 60 min, 90 min, 120 min, 240 min and 360 min. For each sample, three hair switches are prepared. The curl retention values are calculated as follow:

$$C.R.[\%] = \frac{L - L_t}{L - L_0} \times 100$$

L=Length of uncurled Hair (230 mm)
Lo=Length of the curl after drying at the table
Lt=Length of hanging curl in after time t The Curl Retention of one sample is obtained as the mean of the three calculated curl retention values of the three switches.

Every Curl Retention is also measured against a reference (benchmark market polymer).

The results are summarized in table 4:

TABLE 4

Curl Retention in % at 20° C./90% r.H.
(5 wt.-% solids in EtOH, 100% Neutralization1)

| | Time [min] | | | | | | | | |
|---|---|---|---|---|---|---|---|---|---|
| Product | 0 | 15 | 30 | 45 | 60 | 90 | 120 | 240 | 360 |
| Acrylic polymer emulsion according to the invention (TILAMAR ® Fix A 140[1]) | 92.5 | 89.3 | 82.9 | 78.6 | 71.2 | 64.8 | 60.6 | 56.3 | 53.1 |
| Reference | 87.8 | 83.3 | 73.3 | 66.7 | 60 | 53.3 | 50 | 44.4 | 40.0 |

[1]Acrylic emulsion polymer according to example 1

It is clear to be seen, that the acrylic emulsion polymer according to the invention, especially on long term, performs better than a market benchmark taken as reference, i.e. an acrylate emulsion polymer consisting of MAA, tert-butyl acrylate and EA (Luvimer® P100).

EXAMPLE 5

Propellant Compatibility

Add 20 mL of 5 wt.-% (solids) TILAMAR® Fix A140 (acrylic emulsion polymer according to example 1) polymer solution in ethanol (100% neutralization level) into the test tube. Close the glass. Fill in propellant via the aerosol valve (can-to-can).
Propellants: Propane/Butane 2.5 bar, respectively DME at 20° C.
Test criteria: One or two phases
Clear, no clouds, no precipitation
Results: Cloud point at 45% propane/butane (at 5% solids). Clear until 32% DME (at 5% solids). No precipitation observed These results show that the acrylic emulsion polymers according to the invention exhibit a broad propellant compatibility.

EXAMPLE 6

Sensory Performance Assessment

VOC 55 pump sprays were tested by sensory on hair switches and evaluated for tackiness during drying.
Preparation of the Switches
For the tests, medium brown hair switches were used from Demeo Brothers, N.Y. Prior to use, all switches were washed twice with a cleansing shampoo (10% Sodium Laureth sulphate, 4% Sodium Chloride, 0.5% Sodium benzoate, Water, Citric acid to pH=5) and dried overnight in a climate room at 20° C./65% rel. humidity.
Preparation of the VOC 55 Polymer Compositions
5 g (solids) of the respective polymer are dispersed in a mixture of 55 g ethanol, 31.43 g of water and the calculated amount of AMP for complete neutralisation (see table 2 above). The mixtures are stirred till they are clear.
Application of the Polymers to Hair and Detection of the Performance Parameters
10 lifts of the respective VOC 55 polymer composition are applied to the hair switches with a pump spray applicator (0.07 g/lift). The switches were treated and evaluated in a climate room (20° C./65% rel. humidity).
For treatment, the switches were taken with the left hand at the rubberized end ("roots"), and the pump sprays were applied from a distance of 25 cm to the dry hair switch so evenly as possible following the pattern "roots-tip-roots-tip. The switch is placed on the table and the drying evaluation takes place by putting all fingers of the right hand without additional pressure onto the switch, which is fixed at the rubberized end with the left hand, at second 1. The contact pressure is approx. 250 g. The hand is lifted and putted with a frequency of 1 second. During this process, the polymer starts to dry and becomes tacky, which is detected by gluing on the fingers. When the polymer loses tackiness, it does not glue anymore at the fingers. The whole process is followed with a clock. Additionally, the strengths of tackiness is evaluated qualitatively and ranked with "weak" (very slightly tacky), to "strong" (=glue). The result of this evaluation is shown in table 5.

TABLE 5

Results of the evaluation of tackiness and drying time

| Acrylic emulsion polymer | Start of Sticking | Time to Dry | Tackiness |
|---|---|---|---|
| Reference (Luvimer ® 100P) | 10 s | 50 s | Medium |
| Acrylate emulsion polymer according to example 1 | 4 s | 20 s | Weak |

As can be retrieved from the results outlined in table 5, the acrylic polymer emulsion according to the invention exhibits a very short drying time combined with a very low tackiness compared to the reference.

Sensory Test of Aerosol Hairsprays

The following Aerosol Spray formulations 8 table 6) were tested in a Sensory Test on Hair Swatches:

TABLE 6

| Ingredient Name | INCI | Spray 1 % w/w | Spray 2 % w/w | Spray 3 % w/w |
|---|---|---|---|---|
| Ethanol abs. | Alcohol | 53.2 | 44.4 | 35.52 |
| Acrylate emulsion polymer according to example 1(a) | Acrylates Copolymer | 6.00 | 5.00 | 4.00 |
| AMP-Ultra PC 2000 | Aminomethyl Propanol | 0.59 | 0.50 | 0.40 |
| PARSOL ® MCX | Ethylhexyl methoxycinnamate | 0.06 | 0.05 | 0.04 |
| Dow Corning 193 Fluid | PEG-12 Dimethicone | 0.06 | 0.05 | 0.04 |
| DME | Dimethyl ether | 40 | 50 | 60 |

All sprays were applied to hair swatches [Spraying time 3 sec]. The degrees of hold and the drying time/tackiness were rated by 5 different panelists. The results are outlined in Table 7.

TABLE 7

| Nr. | Ratio Bulk/DME | Feeling/Tackiness of the Hair tresses | Stiffness next day (o/n RT) |
|---|---|---|---|
| Spray 3 | 40%/60% | Medium tackiness, fast drying; no visible droplets | Soft feel, firm hold |
| Spray 2 | 50%/50% | Some droplets visible, medium tacky | Soft feel, strong hold |
| Spray 1 | 60%/40% | Fast drying; no visible droplets | Ultra hold |

As can be retrieved the sprays comprising the acrylic polymer emulsion according to the invention exhibits excellent perceivable hold levels combined with a soft feel.

EXAMPLE 7

Formulations

The acrylic emulsion polymers according to the invention such as in particular TILAMAR® Fix A140 (Acrylic emulsion polymer according to example 1) preserved with 50 ppm methylisothiazoline exhibit a unique product form, superior high humidity curl retention, excellent propellant compatibility, easy handling and a natural feel on hair. Thus, the acrylic emulsion polymers according to the invention such as in particular TILAMAR® Fix A140 can be incorporated into a great variety of product forms as illustrated below without being limited thereto:

7.1. VOC Pump Sprays

| No | Ingredients | INCI Name | VOC 80 | VOC 55 wt.-% | High VOC |
|----|----|----|----|----|----|
| 1 | Ethanol | Alcohol | 80 | 55 | Ad 100 |
| 2 | Water demin. | Aqua | Ad 100 | Ad 100 | |
| 3 | Acrylic emulsion polymer according to the invention, in particular TILAMAR ® Fix A140 | Acrylates Copolymer | 12.5 | 10* | 7.5 |
| 4 | AMP-95 | Aminomethyl Propanol | 1.06 | 1.38 | 0.75 |
| 5 | PARSOL ® 340 | Octocrylene | 0.10 | — | |
| 6 | PARSOL ® MCX | Ethylmethoxycinnamate | — | 0.15 | 0.10 |
| 7 | D-PANTHENOL 75 L | Panthenol | 0.10 | 0.10 | 0.10 |
| 8 | PEG-12 Dimethicone | PEG-12 Dimethicone | 0.15 | — | |
| 9 | Phenyl Trimethicone | Phenyl Trimethicone | — | 0.15 | |
| 10 | Fragrance | Fragrance | 0.20 | 0.20 | 0.15 |

*based on a 40% solid content

Procedure: Mix Pos. 1 to Pos. 10.

7.2. Solid Styling Wax

| No | Name | INCI Name | wt.-% |
|----|----|----|----|
| 1 | Water demin. | Aqua | Ad 100 |
| 2 | Isoceteth-20 | Isoceteth-20 | 22.00 |
| 3 | PEG-7 Glyceryl Cocoate | PEG-7 Glyceryl Cocoate | 10.00 |
| 4 | Acrylic emulsion polymer according to the invention, in particular TILAMAR ® Fix A140 | Acrylates Copolymer | 6.00* |
| 5 | Hydrogenated Polydecene | Hydrogenated Polydecene | 6.00 |
| 6 | Glycerin | Glycerin | 4.00 |
| 7 | Quaternium-26 (58%) in Propylene Glycol | Quaternium-26 (58%) in Propylene Glycol | 2.00 |
| 8 | AMP-95 | Aminomethyl Propanol | 1.27 |
| 9 | Propylparabene | Propylparabene | 0.20 |
| 10 | Fragrance | Fragrance | 1.00 |

*based on a 40% solid content

Procedure:

Mix Pos. 1 and Pos. 8, and heat them up to at 60° C. Add Pos. 4 and stir until a clear solution has been formed. Dissolve Pos. 9 in Pos. 6 under heating. Add Pos. 2, 3, 5, 7 and the Glycerin solution of Pos. 9 to the polymer solution and heat the solution up to 80° C. After 10 min, cool down to 40° C., add the fragrance with stirring and fill the mass into a jar. After several hours, the solid wax is formed.

7.3. Fibre Styling Pomade

| No | Name | INCI Name | wt.-% |
|----|----|----|----|
| 1 | Water | Aqua | Ad 100 |
| 2 | Acrylic emulsion polymer according to the invention, in particular TILAMAR ® Fix A140 | Acrylates Copolymer | 10.00* |
| 3 | AMP-95 | Aminomethyl Propanol | 1.27 |
| 4 | Sorbitol 70% | Sorbitol 70% | 4.00 |
| 5 | PEG-90M | PEG-90M | 0.50 |
| 6 | Methylparabene | Methylparabene | 0.25 |
| 7 | PEG 150/Stearyl Alcohol/SMDI Copolymer (19% in water) | PEG 150/Stearyl Alcohol/SMDI Copolymer (19% in water) | 2.20 |
| 8 | Lanolin | Lanolin | 3.00 |
| 9 | Cetyl Dimethicone | Cetyl Dimethicone | 3.00 |
| 10 | Dicaprylyl Carbonate | Dicaprylyl Carbonate | 7.00 |
| 11 | Propylparabene | Propylparabene | 0.20 |
| 12 | Fragrance | Fragrance | 1.00 |
| 13 | Glycol Distearate | Glycol Distearate | 3.00 |
| 14 | Cyclopentasiloxene & Dimethicone Crosspolymer | Cyclopentasiloxene & Dimethicone Crosspolymer | 2.40 |

*based on a 40% solid content

7.4. Styling Cream

| No | Name | INCI Name | wt.-% |
|---|---|---|---|
| 2 | Water | Aqua | Ad 100 |
| 3 | Acrylic emulsion polymer according to the invention, in particular TILAMAR ® Fix A140 | Acrylates Copolymer | 13.75* |
| 4 | PEG 150/Stearyl Alcohol/SMDI Copolymer (19% in water) | PEG 150/Stearyl Alcohol/SMDI Copolymer (19% in water) | 2.20 |
| 5 | Acrylic Acid/VP-Crosspolymer | Acrylic Acid/VP-Crosspolymer | 1.20 |
| 6 | AMP Ultra PC 2000 | Aminomethyl Propanol | 1.07 |
| 7 | Fragrance | Fragrance | 0.35 |
| 8 | Styrene/Acrylates Copolymer (40% in water) | Styrene/Acrylates Copolymer (40% in water) | 0.20 |
| 9 | Silicone Quaternium-16 & Undeceth-11 & Butyloctanol & Undeceth-5 | Silicone Quaternium-16 & Undeceth-11 & Butyloctanol & Undeceth-5 | 1.20 |
| 10 | Ethyl Panthenol | Panthenyl Ethyl Ether | 0.25 |
| 11 | Methylisothiazolinone (10% in Propylene Glycol) | Methylisothiazolinone (10% in Propylene Glycol) | 0.10 |
| 12 | AMP Ultra PC 2000 to adjust pH | Aminomethyl Propanol | 0.20 |
| 13 | PEG-90M | PEG-90M | 0.10 |

*based on a 40% solid content

7.5. Fine Modelling Sprizz

| No | Name | INCI Name | wt.-% |
|---|---|---|---|
| 1 | Ethanol | Alcohol denat. | 25.00 |
| 2 | Water demin. | Aqua | Ad 100 |
| 3 | Acrylic emulsion polymer according to the invention, in particular TILAMAR ® Fix A140 | Acrylates Copolymer | 9.50* |
| 4 | Acrylic Acid/VP-Crosspolymer | Acrylic Acid/VP-Crosspolymer | 0.95 |
| 5 | Silicone Quaternium-16 & Undeceth-11 & Butyloctanol & Undeceth-5 | Silicone Quaternium-16 & Undeceth-11 & Butyloctanol & Undeceth-5 | 2.20 |
| 6 | AMP-95 | Aminomethyl Propanol | 0.74 |
| 7 | Fragrance | Fragrance | 0.20 |
| 8 | PARSOL SLX | Polysilicone-15 | 0.25 |
| 9 | AMP-95 to adjust pH | Aminomethyl Propanol | q.s. |
| 10 | Ethyl Panthenol | Panthenyl Ethyl Ether | 0.20 |
| 11 | Silica & Titanium Dioxide (EU: CI 77891) & Tin Oxide (EU: CI 77861) | Silica & Titanium Dioxide (EU: CI 77891) & Tin Oxide (EU: CI 77861) | 0.10 |

*based on a 40% solid content

Procedure:
Mix Pos. 1-5 and add Pos. 6 till a homogenous mass has been formed. Add Pos. 7&8, adjust pH with Pos. 9 to 7.7 -> Viscosity = 2000 mPas; finally add Pos. 10& 11 and water to 100%.

7.6. Aerosol Hairspray "Strong Hold"

| No | Name | INCI Name | wt.-% |
|---|---|---|---|
| 1 | Ethanol | Alcohol denat. | Ad 100 |
| 2 | AMP-95 | Aminomethyl Propanol | 1.27 |
| 3 | Acrylic emulsion polymer according to the invention, in particular TILAMAR ® Fix A140 | Acrylates Copolymer | 15.00* |
| 4 | D-PANTHENOL 75 L | Panthenol | 0.18 |
| 5 | Neo Heliopan E 1000 | Isoamyl p-Methoxycinnamate (Amiloxate; USAN) | 0.09 |
| 6 | Fragrance | Fragrance | 0.18 |
| 7 | PEG-12 Dimethicone | PEG-12 Dimethicone | 0.18 |

*based on a 40% solid content

Procedure:
This solution is bottled in an appropriate can (aluminium, tinplate), crimped with an aerosol valve and a propellant is added. The propellant, the ratio of effective solution: propellant and the actuator are chosen according to the product requirements as spray rate, spray pattern, particle size and particle size distribution. A typical composition would be: 60% Effective Solution; 40% propane/butane 2.5 bar (high VOC) or 55% effective solution & 45% HF 152A for a water-freeVOC.55 Hairspray.

7.7. Pump Shine & Hold Hair Spray with Natural Feel

| Phase | Ingredients | INCI Name | wt.-% |
|---|---|---|---|
| A | Ethanol | Alcohol denat. | 25.00 |
| | AMP Ultra PC 2000 | Aminomethyl Propanol | 0.98 |
| | Acrylic emulsion polymer according to the invention, in particular TILAMAR ® Fix A140 | Acrylates Copolymer | 11.5* |
| B | Ethanol | Alcohol denat. | Ad 100 |
| | PARSOL ® MCX | Ethylhexyl Methoxycinnamate (Octinoxate; USAN) | 0.10 |
| | Ethyl Panthenol | Panthenyl Ethyl Ether | 0.18 |
| | Pö Headstrong 167170 | Perfume | 0.23 |
| | ARGAN OIL | *Argania Spinosa* Kernel Oil | 0.10 |
| | Citrofol ® AL | Triethyl Citrate | 0.10 |
| C | Water dem. | Aqua | 11.00 |

*based on a 40% solid content

Procedure:
Part A, with stirring: Blend ethanol with AMP PC 2000. Add TILAMAR ® Fix A140 and stir until uniform. This part must be clear. Part B, with stirring: Add ethanol part II into the solution. Add step by step all other ingredients and stir until. Part C, with stirring: Add water into the solution. The solution must be clear.

7.8. Chic Shine Hairspray Luxurious Gloss and Addictive Shine

| Phase | Ingredients | INCI Name | wt.-% |
|---|---|---|---|
| A | Ethanol | Alcohol | 15.00 |
|   | AMP Ultra PC 2000 | Aminomethyl Propanol | 0.71 |
|   | Acrylic emulsion polymer according to the invention, in particular TILAMAR ® Fix A140 | Acrylates Copolymer | 8.4* |
| B | Ethanol | Alcohol | Ad 100 |
|   | Ethyl Panthenol | Panthenyl Ethyl Ether | 0.10 |
|   | PARSOL ® MCX | Ethylhexyl Methoxycinnamate (Octinoxate; USAN) | 0.10 |
|   | Pö Headstrong 167170 | Parfume | 0.14 |
|   | ARGAN OIL | *Argania Spinosa* Kernel Oil | 0.10 |
|   | Citrofol ® AL | Triethyl Citrate | 0.06 |
|   | Water dem. | Aqua | 1.20 |
| C | Propane/Butane 2.5 | Propane/Butane 2.5 | 40.00 |

*based on a 40% solid content
Procedure:
Part A, with stirring: Blend ethanol with AMP PC 2000. Add TILAMAR ® Fix A 140 and stir until uniform. This part must be clear. Part B, with stirring: Add ethanol part II into the solution. Add step by step all other ingredients and stir until. Part C, Add propane/butane

7.9. Ringing Gel Glossy Pomade with Vitamin E

| Phase | Ingredients | INCI Name | wt.-% |
|---|---|---|---|
| A | Water dem./part I | Water (Aqua) | 35.00 |
|   | Acrylic emulsion polymer according to the invention, in particular TILAMAR ® Fix A140 | Acrylates Copolymer | 11.00* |
|   | AMP Ultra PC 2000 | Aminomethyl Propanol | 0.97 |
| B | Cetiol HE | PEG-7 Glyceryl Cocoate | 17.00 |
|   | Eumulgin B3 | Ceteareth-30 | 22.00 |
|   | Tegosoft M | Isopropyl Myristate | 4.00 |
| C | Water dem./part II | Water (Aqua) | Ad 100 |
|   | Glycerin | Glycerin | 4.00 |
|   | FD & C Blue 1 | Blue 1 (CI 42090) | q.s. |
|   | Ronastar Noble Sparks | Calcium Aluminium Borsilikat & Silica & Titanium Dioxide (CI 77891) & Tin Oxide (CI 77861) | 0.001 |
| D | PÖ Headstrong 167170 | Parfume | 1.00 |
|   | Neolone 950 Preservative | Methylisothiazolinone | 0.10 |
|   | VITAMIN E ACETATE | Tocopheryl Acetate | 0.25 |

*based on a 40% solid content
Procedure:
Part A, with stirring: Blend water part I with AMP PC 2000. Add TILAMAR ® Fix A140 and stir until uniform. Heat to 80° C. This part must be clear. Part B, with stirring: In a separate vessel combine the Cetiol HE, Eumulgin B3 and Tegosoft M. Heat to the same temperature. With adequate mixing add step 2 to step 1 and maintain at 80° C. for 3-5 minutes. Adding step by step ingredients part C. Reduce mixing speed and cool to room temperature. Add the perfume, preservative and vitamin E at 50° C.-55° C. and continue cooling.

7.10. Elastic Flexible Hold Hairspray with UV Protection and Pro-Vitamin B5

| Phase | Ingredients | INCI Name | wt.-% |
|---|---|---|---|
| A | Ethanol | Alcohol | 25.00 |
|   | AMP Ultra PC 2000 | Aminomethyl Propanol | 1.27 |
|   | Acrylic emulsion polymer according to the invention, in particular TILAMAR ® Fix A140 | Acrylates Copolymer | 15.00* |
| B | Ethanol | Alcohol | Ad 100 |
|   | D-PANTHENOL 75 L | Panthenol | 0.18 |
|   | Neo Heliopan, Type E 1000 | Isoamyl p-Methoxycinnamate (Amiloxate; USAN) | 0.09 |
|   | Pö Color Express 351580 | Parfum | 0.18 |
|   | Dow Corning 193 | PEG-12 Dimethicone | 0.18 |

*based on a 40% solid content
Procedure:
Part A, with stirring: Blend ethanol with AMP PC 2000. Add TILAMAR ® Fix A140 and stir until uniform. This part must be clear. Part B, with stirring: Add ethanol part II into the solution. Add step by step all other ingredients and stir until.

7.11. Chic Shine Hairspray Luxurious Gloss and Addictive Shine

| Phase | Ingredients | INCI Name | wt.-% |
|---|---|---|---|
| A | Ethanol | Alcohol | 25.00 |
|   | AMP Ultra PC 2000 | Aminomethyl Propanol | 1.19 |
|   | Acrylic emulsion polymer according to the invention, in particular TILAMAR ® Fix A140 | Acrylates Copolymer | 14.00* |
| B | Ethanol | Alcohol | 65.37 |
|   | Ethyl Panthenol | Panthenyl Ethyl Ether | 0.17 |
|   | PARSOL ® MCX | Ethylhexyl Methoxycinnamate (Octinoxate; USAN) | 0.17 |
|   | Pö Headstrong 167170 | Parfume | 0.23 |
|   | ARGAN OIL | *Argania Spinosa* Kernel Oil | 0.17 |
|   | Citrofol ® AL | Triethyl Citrate | 0.10 |
|   | Water dem. | Aqua | 2.00 |

*based on a 40% solid content
Procedure:
Part A, with stirring: Blend ethanol with AMP PC 2000. Add TILAMAR ® Fix A140 and stir until uniform. This part must be clear. Part B, with stirring: Add ethanol part II into the solution. Add step by step all other ingredients and stir until.

7.12. Elastic Flexible Hold Hairspray with UV Protection and Pro-Vitamin B5

| Phase | Ingredients | INCI Name | wt.-% |
|---|---|---|---|
| A | Ethanol | Alcohol | 17.50 |
|   | AMP Ultra PC 2000 | Aminomethyl Propanol | 0.89 |
|   | Acrylic emulsion polymer according to the invention, in particular TILAMAR ® Fix A140 | Acrylates Copolymer | 10.5* |
| B | Ethanol | Alcohol | Ad. 100 |
|   | D-PANTHENOL 75 L | Panthenol | 0.13 |
|   | Neo Heliopan, Type E 1000 | Isoamyl p-Methoxycinnamate (Amiloxate; USAN) | 0.06 |
|   | Pö Color Express 351580 | Parfum | 0.13 |
|   | Dow Corning 193 | PEG-12 Dimethicone | 0.13 |
| C | Propane/Butane 2.5 | Propane/Butane 2.5 | 30.00 |

*based on a 40% solid content
Procedure:
Part A, with stirring: Blend ethanol with AMP PC 2000. Add TILAMAR ® Fix A140 and stir until uniform. This part must be clear. Part B, with stirring: Add ethanol part II into the solution. Add step by step all other ingredients and stir until. Part C. Add propane/butane.

7.13. Chic Shine Hairspray Luxurious Gloss and Addictive Shine

| Phase | Ingredients | INCI Name | wt.-% |
|---|---|---|---|
| A | Ethanol | Alcohol denat. | 17.50 |
|   | AMP Ultra PC 2000 | Aminomethyl Propanol | 0.83 |
|   | Acrylic emulsion polymer according to the invention, in particular TILAMAR ® Fix A140 | Acrylates Copolymer | 9.8* |
| B | Ethanol | Alcohol | Ad 100 |
|   | Ethyl Panthenol | Panthenyl Ethyl Ether | 0.12 |

-continued

| Phase | Ingredients | INCI Name | wt.-% |
|---|---|---|---|
| | PARSOL ® MCX | Ethylhexyl Methoxycinnamate (Octinoxate; USAN) | 0.12 |
| | Pö Headstrong 167170 | Parfume | 0.16 |
| | ARGAN OIL | *Argania Spinosa* Kernel Oil | 0.12 |
| | Citrofol ®AL | Triethyl Citrate | 0.07 |
| | Water dem. | Aqua | 1.40 |
| C | Propane/Butane 2.5 | Propane/Butane 2.5 | 30.00 |

*based on a 40% solid content

Procedure:

Part A, with stirring: Blend ethanol with AMP PC 2000. Add TILAMAR ® Fix A140 and stir until uniform. This part must be clear. Part B, with stirring: Add ethanol part II into the solution. Add step by step all other ingredients and stir until. Part C: after bottling and crimping, add propane/butane.

7.14. Elastic Flexible Hold Hairspray VOC 55

| Phase | Ingredients | INCI Name | wt.-% |
|---|---|---|---|
| A | Ethanol | Alcohol | 17.50 |
| | AMP Ultra PC 2000 | Aminomethyl Propanol | 0.89 |
| | Acrylic emulsion polymer according to the invention, in particular TILAMAR ® Fix A140 | Acrylates Copolymer | 10.50* |
| B | Water | Aqua | Ad 100 |
| | D-PANTHENOL 75 L | Panthenol | 0.13 |
| | PARSOL ® MCX | Ethylhexyl Methoxycinnamate (Octinoxate; USAN) | 0.06 |
| | Pö Color Express 351580 | Parfum | 0.13 |
| | Dow Corning 193 | PEG-12 Dimethicone | 0.13 |
| C | Dimethylether (DME) | Dimethylether | 35.00 |

*based on a 40% solid content

Procedure:

Part A, with stirring: Blend ethanol with AMP PC 2000. Add TILAMAR ® Fix A140 and stir until uniform. This part must be clear. Part B, with stirring: Add water part II into the solution. Add step by step all other ingredients and stir until. Part C: After bottling and crimping, add DME.

EXAMPLE 8

The polymers according to the resent invention such as in particular TILAMAR® Fix A140 can also be easily combined with other commercially available hair styling polymers in order to further improve the performance. Some basic formulation examples are given in the following part without being limited thereto.

8.1. Combination with Hair Styling Polymers Available at Dow:

The given concentrations are examples and could be varied according to requirements in ranges of 1-10%.

| | | A | B | C |
|---|---|---|---|---|
| Ingredients | INCI Name | wt.-% | | |
| ALCOHOL DENAT. | Alcohol denat. | Ad. 100 | | |
| Acrylic emulsion polymer according to the invention, in particular TILAMAR ® Fix A140 | Acrylates Copolymer | 12.50 (based on a 40% solid content) | | |
| ACUDYNE ™ DHR | Acrylates/Hydroxyesters acrylates Copolymer | 2.65 | — | — |
| ACUDYNE ™ LT-120 | Acrylates/C 1-2 Succinates/Hydroxyacrylates Copolymer | — | 2.65 | — |
| ACUDYNE ™ 180 | Acrylates/Hydroxyesters acrylates Copolymer | — | — | 2.65 |
| AMP Ultra PC 2000 | Aminomethyl Propanol | 1.30 | 1.34 | 1.32 |
| D-PANTHENOL | Panthenol | 0.15 | 0.15 | 0.15 |
| DOW CORNING 193 | PEG-12 Dimethicone | 0.15 | 0.15 | 0.15 |

8.2. Combination with Hair Styling Polymers Available at BASF:

The given concentrations are examples and could be varied according to requirements in ranges of 1-10%.

| | | 1 | 2 | 3 | 4 | 5 | 6 | 7 |
|---|---|---|---|---|---|---|---|---|
| Ingredients | INCI Name | wt.-% | | | | | | |
| ALCOHOL DENAT. | Alcohol denat. | Ad 100 | | | | | | |
| Acrylic emulsion polymer according to the invention, in particular TILAMAR ® Fix A140 | Acrylates Copolymer | 12.50 (based on a 40% solid content) | | | | | | |
| LUVIMER ® P100 | Acrylates Copolymer | 1.2 | | | | | | |
| LUVIMER ® PRO 55 | Acrylates Copolymer | | 3.25 | | | | | |
| LUVISKOL ® VA 37E | VP/VA Copolymer | | | 2.4 | | | | |
| LUVISKOL ® PLUS | Polyvinylcaprolactam | | | | 3.0 | | | |
| LUVISET ® CAN | VA/Crotonates/Vinyl neodecanoate Copolymer | | | | | 1.2 | | |
| LUVISET ® CA 66 | Vinyl acetate/Crotonic acid copolymer | | | | | | 1.2 | |
| LUVISET ® SHAPE | Polyacrylate-22 | | | | | | | 3.45 |
| AMP Ultra PC 2000 | Aminomethyl Propanol | Ad. to 90-100% neutralisation level of polymers | | | | | | |
| D-PANTHENOL | Panthenol | 0.15 | | | | | | |
| DOW CORNING 193 | PEG-12 Dimethicone | 0.15 | | | | | | |

8.2. Continued

The given concentrations are examples and could be varied according to requirements in ranges of 1-10%.

| Ingredients | INCI Name | 8 | 9 | 10 | 11 | 12 | 13 |
|---|---|---|---|---|---|---|---|
| | | | | wt.-% | | | |
| ALCOHOL DENAT. | Alcohol denat. | Ad 100 | | | | | |
| Acrylic emulsion polymer according to the invention, in particular TILAMAR ® Fix A140 | Acrylates Copolymer | 12.50 (based on a 40% solid content) | | | | | |
| LUVISKOL ® VA 55 I | VP/VA Copolymer (and) Isopropanol | 2.4 | | | | | |
| LUVISKOL ® VA 37 I | VP/VA Copolymer (and) Isopropanol | | 2.4 | | | | |
| ULTRAHOLD ® 8 | Acrylate/acrylamide Copolymer | | | 1.2 | | | |
| ULTRAHOLD ® STRONG | Acrylates/t-Butyl-acrylamide copolymer | | | | 1.2 | | |
| LUVISET ® PUR | Polyurethane-1 | | | | | 4 | |
| LUVIFLEX ® SILK | PEG/PPG 25/25 Dimethicone/Acrylates copolymer | | | | | | 2.4 |
| AMP Ultra PC 2000 | Aminomethyl Propanol | Ad. to 90-100% neutralisation level of polymers | | | | | |
| D-PANTHENOL | Panthenol | 0.15 | | | | | |
| DOW CORNING 193 | PEG-12 Dimethicone | 0.15 | | | | | |

25

8.3 Combination with Hair Styling Polymers Available at Akzonobel:

The given concentrations are examples and could be varied according to requirements in ranges of 1-10%.

| PRODUCT NAME | INCI Name | 1 | 2 | 3 | 4 | 5 | 6 | 7 | 8 | 9 |
|---|---|---|---|---|---|---|---|---|---|---|
| | | | | | wt.-% | | | | | |
| ALCOHOL DENAT. | Alcohol denat. | Ad 100 | | | | | | | | |
| Acrylic emulsion polymer according to the invention, in particular TILAMAR ® Fix A140 | Acrylates Copolymer | 12.50 (based on a 40% solid content) | | | | | | | | |
| AMPHOMER | Octylacrylamide/acrylates/butylaminoethyl methacrylate copolymer | 1.2 | | | | | | | | |
| AMPHOMER LV-71 | Octylacrylamide/acrylates/butylaminoethyl methacrylate copolymer | | 1.2 | | | | | | | |
| AMPHOMER 4961 | Acrylates/octylacrylamide copolymer | | | 1.2 | | | | | | |
| AMPHOMER HC | Acrylates/octylacrylamide copolymer | | | | 1.2 | | | | | |
| RESYN 28-2930 | VA/crotonates/vinyl neodecanoate copolymer | | | | | 1.2 | | | | |
| RESYN XP | Acrylates/octylacrylamide copolymer | | | | | | 1.2 | | | |
| BALANCE 47 | Octylacrylamide/acrylates/butylaminoethyl methacrylate copolymer | | | | | | | 1.2 | | |
| BALANCE CR | Acrylates copolymer | | | | | | | | 2.4 | |
| DYNAMX ® | Polyurethane-14 (and) AMP-acrylates copolymer | | | | | | | | | 4 |
| AMP Ultra PC 2000 | Aminomethyl Propanol | Ad. to 90-100% neutralization level of polymers | | | | | | | | |
| D-PANTHENOL | Panthenol | 0.15 | | | | | | | | |
| DOW CORNING 193 | PEG-12 Dimethicone | 0.15 | | | | | | | | |

8.4 Combination with Hair Styling Polymers Available at Lubrizol:

The given concentrations are examples and could be varied according to requirements in ranges of 1-10%.

| Ingredients | INCI Name | A wt.-% | B wt.-% |
|---|---|---|---|
| ALCOHOL DENAT. | Alcohol denat. | Ad 100 | |
| Acrylic emulsio polymern according to the invention, in particular TILAMAR ® Fix A140 | Acrylates Copolymer | 12.50 (based on a 40% solid content) | |
| Fixate ™ G-100 Polymer | AMP-Acrylates/ Allyl Methacrylate Copolymer | 8.00 | — |
| Fixate ™ Superhold Polymer | Polyacrylate-2 Crosspolymer | — | 5.00 |
| AMP Ultra PC 2000 | Aminomethyl Propanol | Ad. to 90-100% neutralization level of polymers | |
| D-PANTHENOL | Panthenol | 0.15 | |
| DOW CORNING 193 | PEG-12 Dimethicone | 0.15 | |

The invention claimed is:

1. A hair styling method which comprises applying to hair of a person in need of hair styling an effective amount of a hair styling composition comprising an acrylic emulsion polymer which is the emulsion polymerized reaction product of a monomer mixture consisting of 10-30 wt. % methacrylic acid, 5-15 wt. % ethyl acrylate and 60-80 wt. % n-butyl methacrylate, based on 100 wt. % of the monomer mixture, wherein the acrylic emulsion polymer has a total residual monomer content below 500 ppm.

2. The hair styling method according to claim 1, wherein the monomer mixture consists of 15 25 wt.-% of methacrylic acid, 8-12 wt.-% of ethyl acrylate 65-75 wt. % of n-butyl methacrylate, based on 100 wt. % of the monomer mixture.

3. The hair styling method according to claim 1, wherein the monomer mixture consists of 18-23 wt.-% of methacrylic acid, 9-11 wt.-% of ethyl acrylate and 67-72 wt. % of n-butyl methacrylate, based on 100 wt. % of the monomer mixture.

4. The hair styling method according to claim 1, wherein the acrylic emulsion polymer has a molecular weight between 75 and 200 k Dalton and a glass transition temperature between 70-120° C.

5. The hair styling method according to claim 1, wherein the acrylic emulsion polymer is neutralized with 2-amino-2-methyl-1-propanol and has a neutralization level of 100%.

6. The hair styling method according to claim 1, wherein the hair styling composition comprises an aqueous dispersion of the acrylic emulsion polymer and methylisothiazoline, wherein the aqueous dispersion has a solids content of the acrylic emulsion polymer of about 35 to 45 wt.-% and a content of the methylisothiazoline of about 30 to 50 ppm.

7. The hair styling method according to claim 1, wherein the hair styling composition comprises the at least one acrylic emulsion polymer in an amount of 0.01-20 wt.-%, based on the total weight of the cosmetic composition.

8. The hair styling method according to claim 1, wherein the hair styling composition is in the form of a styling cream, styling gel, liquid hair-setting preparation, hair foam or hair-spray.

9. The hair styling method according to claim 1, wherein the hair styling composition is in the form of a VOC 55 composition.

10. The hair styling method according to claim 1, wherein the hair styling composition is an aerosol hairspray.

11. The hair styling method according to claim 1, wherein the total residual monomer content of the emulsion polymer is below 350 ppm.

12. The hair styling method according to claim 1, wherein the total residual monomer content of the emulsion polymer is below 200 ppm.

13. The hair styling method according to claim 1, wherein the emulsion polymer has a total amount of residual n-butyl methacrylate monomer of below 300 ppm.

14. The hair styling method according to claim 13, wherein the total amount of residual n-butyl methacrylate monomer is below 200 ppm.

15. The hair styling method according to claim 13, wherein the total amount of residual n-butyl methacrylate monomer is below 150 ppm.

16. The hair styling method according to claim 1, wherein the emulsion polymer has a total amount of residual methacrylic acid monomer of below 300 ppm.

17. The hair styling method according to claim 16, wherein the total amount of residual methacrylic acid monomer is below 200 ppm.

18. The hair styling method according to claim 16, wherein the total amount of residual methacrylic acid monomer is below 150 ppm.

19. The hair styling method according to claim 1, wherein the emulsion polymer has a total amount of residual ethyl acrylate monomer of below 200 ppm.

20. The hair styling method according to claim 19, wherein the total amount of residual ethyl acrylate monomer is below 100 ppm.

21. The hair styling method according to claim 19, wherein the total amount of residual ethyl acrylate monomer is below 50 ppm.

* * * * *